(12) United States Patent
Larson et al.

(10) Patent No.: US 7,857,777 B2
(45) Date of Patent: Dec. 28, 2010

(54) ELECTRO ACTIVE COMPRESSION BANDAGE

(75) Inventors: Tomas Larson, Sturefors (SE); Landy Toth, Linköping (SE)

(73) Assignee: ConvaTec Technologies Inc., Las Vegas, NV (US)

( * ) Notice: Subject to any disclaimer, the term of this patent is extended or adjusted under 35 U.S.C. 154(b) by 809 days.

(21) Appl. No.: 11/576,936

(22) PCT Filed: Oct. 10, 2005

(86) PCT No.: PCT/EP2005/010886

§ 371 (c)(1), (2), (4) Date: Apr. 9, 2007

(87) PCT Pub. No.: WO2006/040109

PCT Pub. Date: Apr. 20, 2006

(65) Prior Publication Data

US 2008/0195018 A1    Aug. 14, 2008

(30) Foreign Application Priority Data

Oct. 11, 2004  (EP) .................................. 04445107
Oct. 11, 2004  (EP) .................................. 04445108

(51) Int. Cl.
- *A61F 5/00* (2006.01)
- *A61F 2/08* (2006.01)
- *A61N 1/00* (2006.01)
- *A61L 15/00* (2006.01)

(52) U.S. Cl. ...................... 602/13; 602/2; 602/3; 602/9; 602/60; 602/61; 602/62; 602/63; 602/75; 600/13; 600/15; 623/14.13

(58) Field of Classification Search .................. 602/2–3, 602/5, 12, 60–66, 75; 600/16–18, 29–32; 623/14.13
See application file for complete search history.

(56) References Cited

U.S. PATENT DOCUMENTS
3,826,249 A    7/1974    Lee et al.
(Continued)

FOREIGN PATENT DOCUMENTS
EP    1 324 403    7/2003
(Continued)

OTHER PUBLICATIONS
International Search Report for PCT/EP2005/010886, completed on Feb. 7, 2006, mailed on Feb. 16, 2006.
(Continued)

*Primary Examiner*—Patricia M Bianco
*Assistant Examiner*—Brandon Jackson
(74) *Attorney, Agent, or Firm*—John M. Kilcoyne

(57) ABSTRACT

The proposed device includes two segments adapted to enclose a body part in a form-fitting manner. Each segment contains an electroactive-material-based actuator, which is adapted to receive an electrical control signal and in response thereto adjust the actuator's morphology, so as to cause the segment to apply a basic pressure profile to the body part. A pressure transition is adapted to redistribute the basic pressure profiles between the first and second segments. A control signal in respect of the first segment causes the pressure transition system to apply a first adjusted pressure profile to at least part of the second portion of the body part, and vice versa, a control signal in respect of the second segment causes the pressure transition system to apply a second adjusted pressure profile to at least a part of the first portion of the body part.

1 Claim, 8 Drawing Sheets

U.S. PATENT DOCUMENTS

| | | | |
|---|---|---|---|
| 5,172,689 A * | 12/1992 | Wright | 607/104 |
| 5,897,517 A * | 4/1999 | Laghi | 602/62 |
| 5,997,465 A | 12/1999 | Savage et al. | |
| 6,010,471 A | 1/2000 | Ben-Noon | |
| 6,076,013 A * | 6/2000 | Brennan et al. | 607/2 |
| 6,123,681 A | 9/2000 | Brown, III | |
| 6,506,206 B1 | 1/2003 | Guzman et al. | |
| 6,613,350 B1 * | 9/2003 | Zhang et al. | 424/449 |
| 7,022,093 B2 * | 4/2006 | Smith et al. | 602/2 |
| 7,044,924 B1 * | 5/2006 | Roth et al. | 601/151 |
| 7,214,847 B1 * | 5/2007 | Flick | 602/48 |
| 7,491,185 B2 * | 2/2009 | Couvillon, Jr. | 601/148 |
| 2002/0173735 A1 | 11/2002 | Lewis | |
| 2003/0212306 A1 | 11/2003 | Banik | |
| 2009/0299249 A1 * | 12/2009 | Wilkes et al. | 602/42 |

FOREIGN PATENT DOCUMENTS

| | | |
|---|---|---|
| EP | 1 324 406 | 7/2003 |
| SU | 1245312 A1 | 7/1986 |

OTHER PUBLICATIONS

Applicant response to Written Opinion, dated May 2, 2006.

International Preliminary Report on Patentability for corresponding International Application No. PCT/EP2005/010886 completed Apr. 23, 2007.

\* cited by examiner

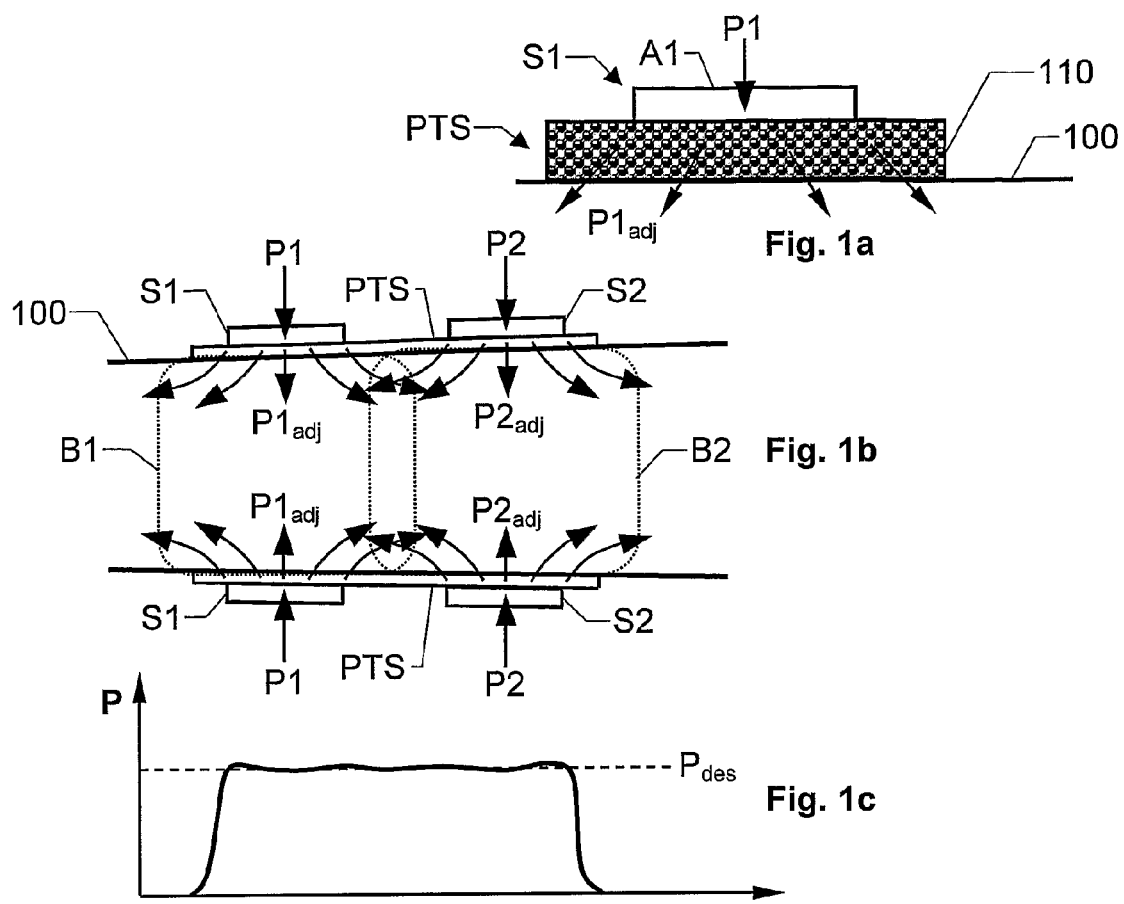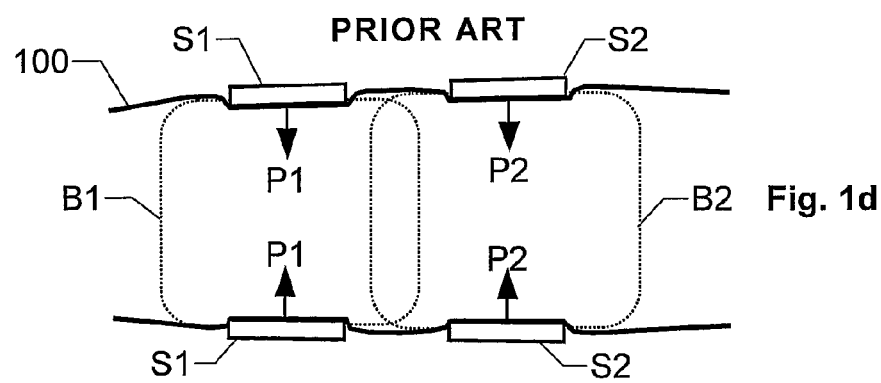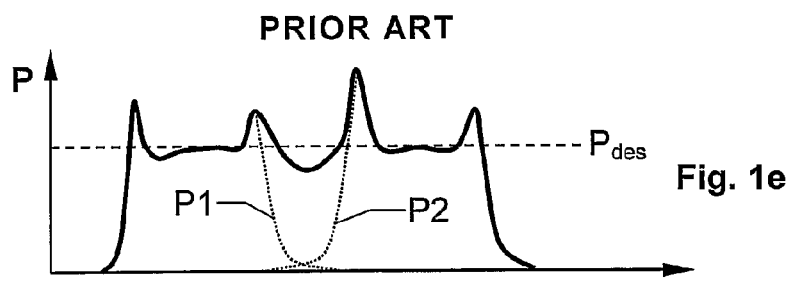

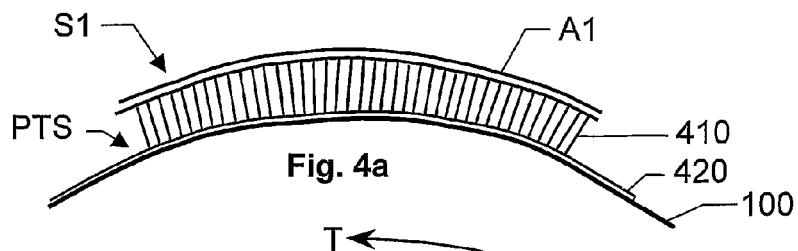
Fig. 4a
Fig. 4b
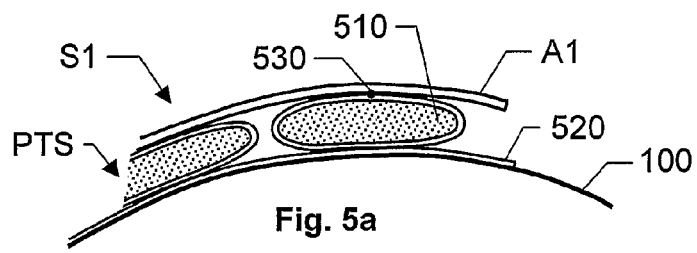
Fig. 5a
Fig. 5b
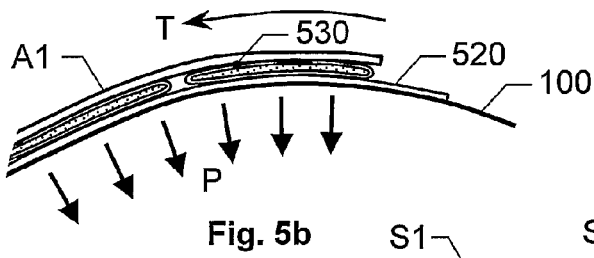
Fig. 6a
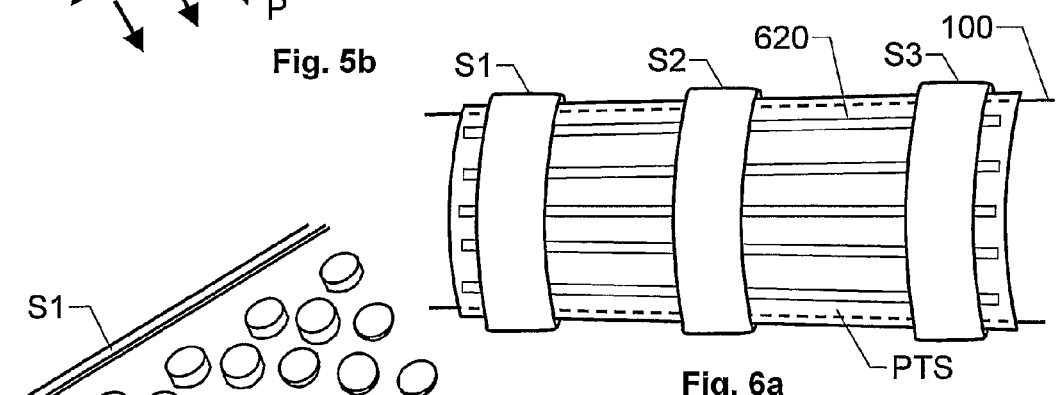
Fig. 6b

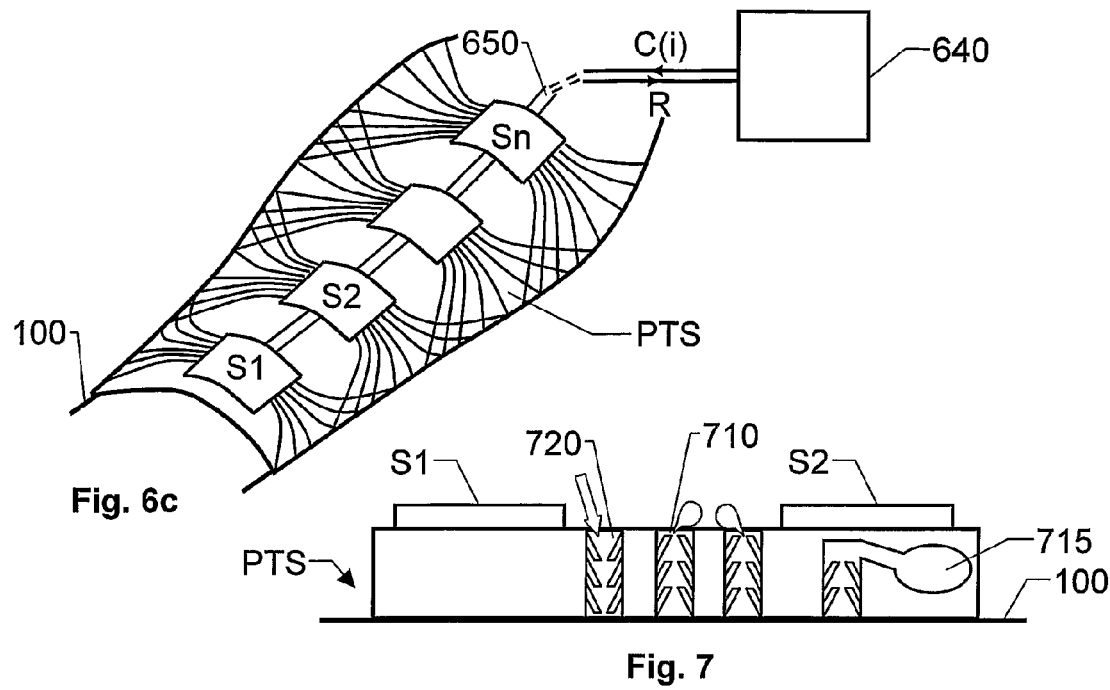
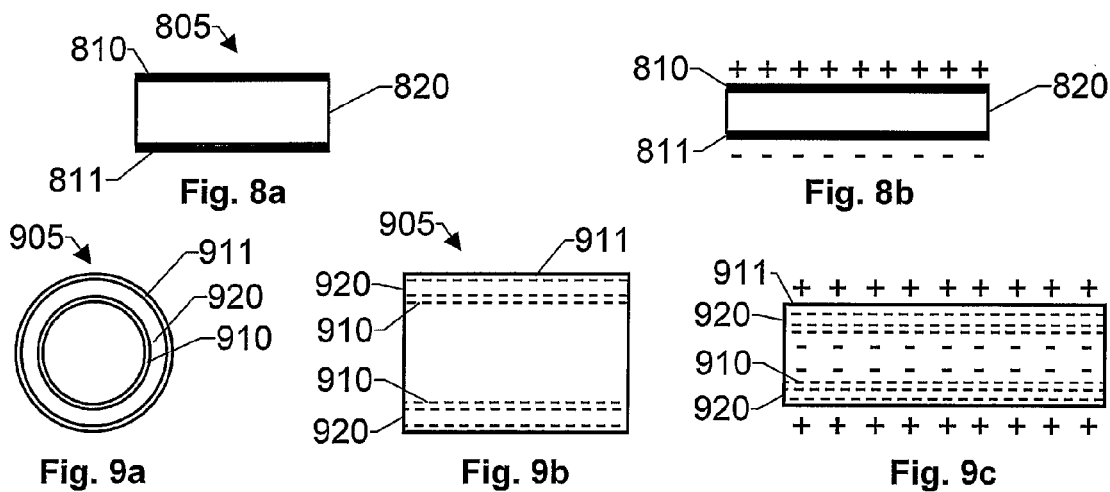
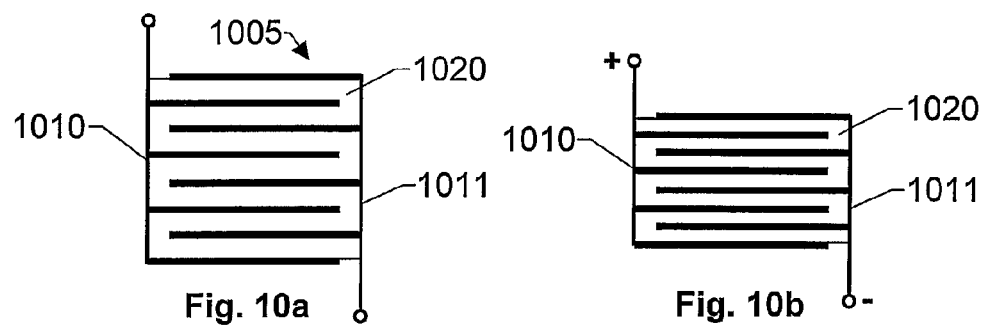

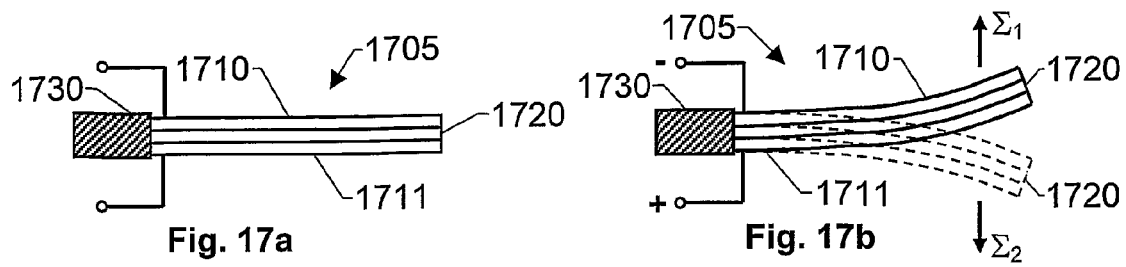
Fig. 17a  Fig. 17b
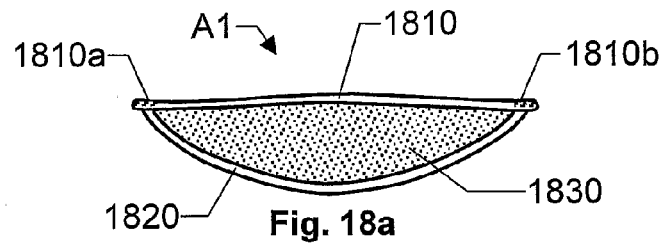
Fig. 18a
Fig. 18b
Fig. 18c
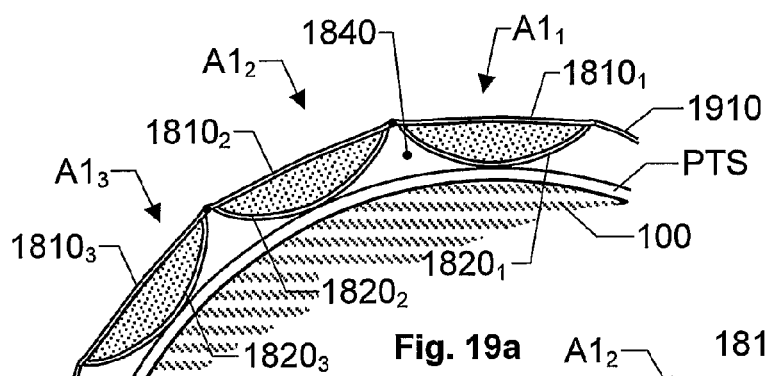
Fig. 19a
Fig. 19b

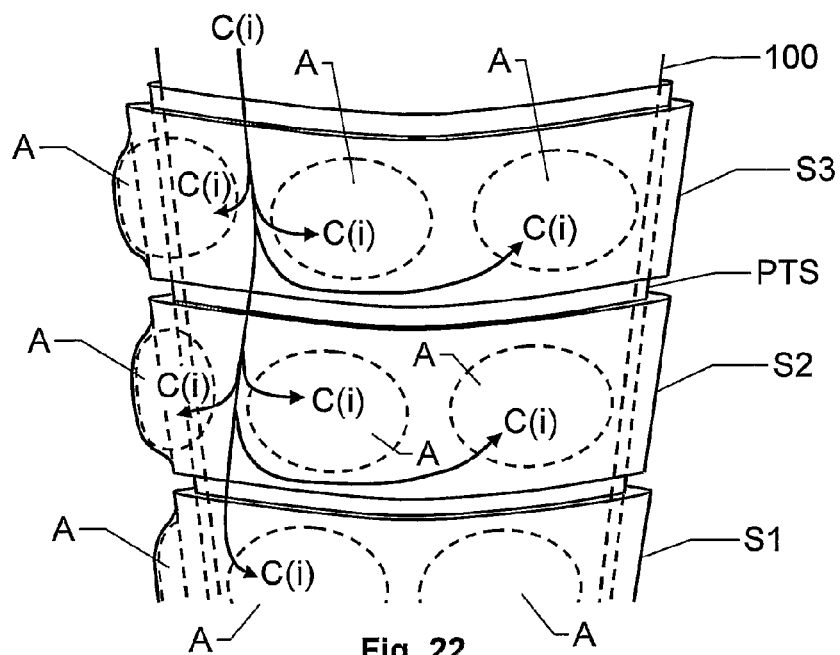
Fig. 22
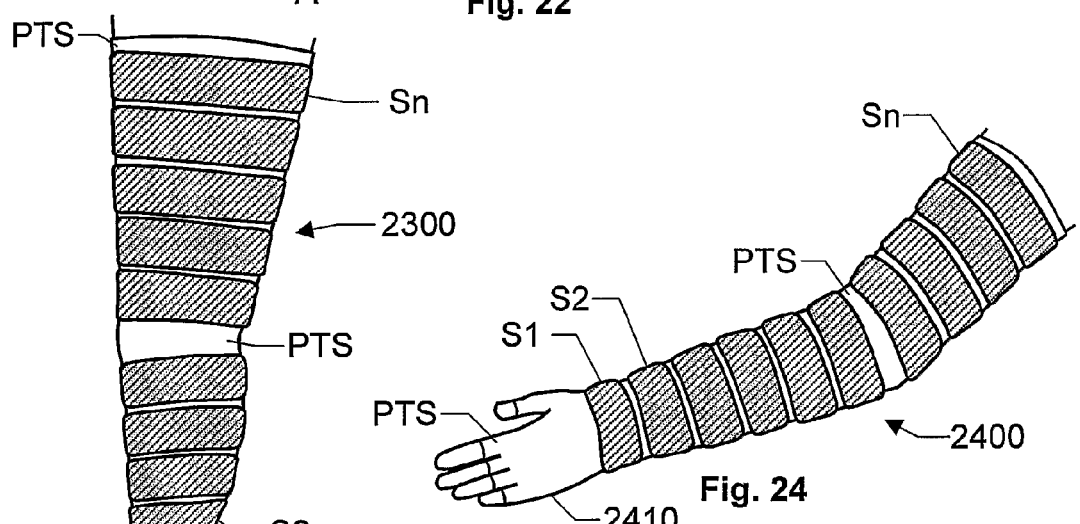
Fig. 23
Fig. 24
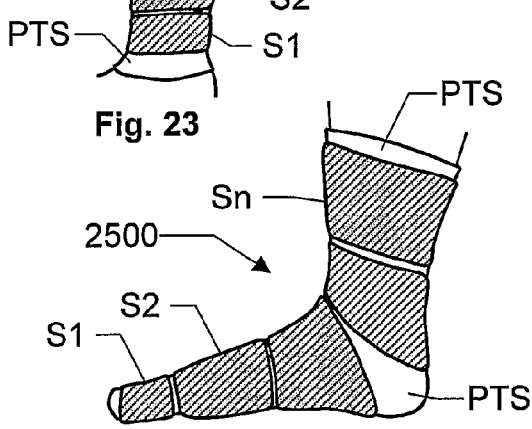
Fig. 25
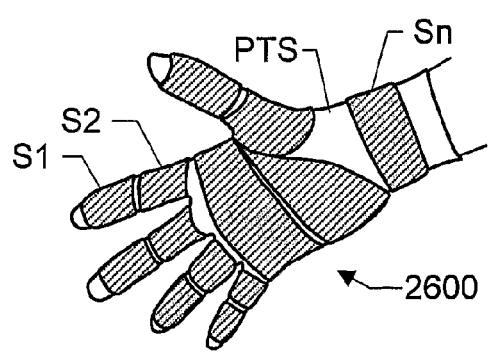
Fig. 26

ELECTRO ACTIVE COMPRESSION BANDAGE

This application is a national stage entry of PCT Application No. PCT/EP05/10886 filed on Oct. 10, 2005, which claims priority to EP04445108.6 and EP04445107.8, both filed Oct. 11, 2004, and each of which are hereby incorporated by reference in their entirety.

THE BACKGROUND OF THE INVENTION AND PRIOR ART

The present invention relates generally to the application of pressure profiles to living tissues. More particularly the invention relates to a device for exerting an external pressure to a human body part according to the preamble of claim 1 and a therapeutic garment according to the preamble of claim 34.

External pressure profiles may be applied to living tissues, e.g. of a person's limb, in order to attain various effects with respect to these tissues. Perhaps the most well known example is the so-called G-suit worn by a pilot to restrict the blood circulation in his/her lower body parts under certain conditions, and thus reduce the risk that an insufficient amount of blood is fed to the pilot's head.

However, also in the medical field there are many examples of situations in which it is relevant/desirable to apply an external pressure to a part of the human body, in order to cure or mitigate a disease or condition. For instance, lymphoedema is a condition where the lymphatic system of a patient has been compromised, thereby resulting in a buildup of lymphatic fluids and proteins in one or more extremities. So far, various approaches have been attempted to control the swelling of the afflicted extremities. The compression-based treatment of lymphoedema is primarily dealt with in three ways, which may be combined to achieve an improved result, compression bandaging, pneumatic compression pumps and massage. The compression bandaging may be further divided into two general approaches: multi-layered lymphatic bandaging and elastic compression garments/bandages. Both these methods are used to statically compress the afflicted limbs, whereas pneumatic compression pumps and massage represent dynamic treatments.

Multi-layered lymphatic bandages are applied to a patient in order to reshape one or more of the patient's limbs. The bandages consist of absorbent layers, padding and short-stretch bandages. The absorbent layers must be custom made by a technician to fit the patient. Moreover, the underlying pressure is unknown after application, and the bandages are there to prevent the limb from further expanding and to breakup proteins with the help of patient movement. Nevertheless, these bandages are associated with numerous problems. During the treatment the bandages must be adjusted many times, for example because the bandages have a static shape and the shape of the limb varies over time. The bandages are also bulky and hot to wear due to the many layers applied to the limb, and therefore the bandages cannot be worn under clothing. Naturally, the therapy for the patient is limited in that the multi-layered lymphatic bandages cannot actively pressurize the body.

Elastic compression bandages are used to statically pressurize an afflicted limb. Here, a caregiver wraps the afflicted limb with a combination of elastic bandages and absorbent layers. The bandages are arranged so as to apply a graduated pressure to the limb. The pressure gradient along the limb is structured such that the highest pressure is at the distal end, and the lowest pressure is located at the proximal end of the limb. Hence, also in this case, the pressure application is static and a qualified person must apply the bandages to ensure that an appropriate pressure is accomplished, particularly since there is no convenient way to accurately measure the pressure applied to the limb. Normally, a constant bandage tension is applied while wrapping the limb, and the pressure graduation is typically a consequence of the limb being thinner at the distal part than at the proximal part. As the limb changes size due to the pressure, and as the bandages creep, the pressure application will decrease. This is true already within hours of applying the bandages.

A pneumatic compression pump device is used to dynamically pressurize limbs of patients. Here, dynamic pressurization is employed both to pump lymphatic fluids from the limb in wave-like, or graduated, pressure profiles and to breakup proteins that collect and harden in the afflicted limb. To generate the wave-like and graduated pressure profiles along the limb, a sleeve portion of the device must have multiple chambers. Each chamber is pressurized at the appropriate time as determined by the treatment prescription. However, the pneumatic compression pump devices are relatively inefficient, and therefore cannot operate from batteries for any significant length of time. In fact, it is normally required that the device be connected to mains power, and as a further consequence that the patient be stationary during the treatment. Since the pneumatic compression pump device is airtight, heat produced by the patient is accumulated in the device. Thus, the device can only be used for comparatively short durations before it becomes too uncomfortable for the patient. Although the device can dramatically reduce oedema during treatment, after use, static compression bandages (or equivalent) must be applied to prevent the fluids from draining back into the afflicted limb. Additionally, the device is noisy, the air-pressure measurements used to infer pressure applied to the limb can be inaccurate, and unintentionally high pressure levels may harm the patient.

A qualified massage therapist/clinician may also apply various forms of massage to a patient. Such massage techniques are highly technical and require significant training to perform. Thus, the outcome of the treatment depends very much on the skill of the clinician.

U.S. Pat. No. 5,997,465 describes a device for exerting an external pressure on a human body, wherein the device surrounds a body part with a comfortable fit. The device includes memory material components, which alter their shape in response to an electric signal. Thereby, in a contracted state, these components may squeeze the body part, for example to prevent pooling of blood in the body part of a pilot when subjected to G-forces. Then, in a non-contracted state (i.e. when no electric signal is present) the memory material components resume their original shape, and the squeezing ceases. The electrical control proposed in this document overcomes some of the shortcomings associated with the above-described dynamic procedures, i.e. the pneumatic compression pump devices and massage forms. However, the solution is still inadequate for many medical applications. For instance, the skin of a patient is often compromised due to various medical conditions. In addition, the health of the patient's skin may lack elasticity, strength and resilience. Therefore, extreme care must be given to ensure that the pressure profile applied to the patient is medically safe. For instance, if highly localized pressures are applied for long periods of time, the tissues can tear and/or pressure ulcers may be formed. Moreover, if subjected to repeated rubbing, the skin can chafe, or even rip. Additionally, the medical treatments often require that the garments be worn for prolonged periods of time during which pressure and/or repeated pressure pulsation may be applied. Such activities further increase the risk of damage being caused to the patient's skin. Some medical applications may also require that the pressure profiles be variable over a very wide range, for example to promote fluid flow in superficial and interstitial tissues. Sometimes it is desired that the pressure profile emulate the naturally occurring function of a healthy body part.

The document EP 1 324 403 describes a motion augmentation solution, wherein an electroactive elastic actuator assists a patient to bend or unbend a joint. Although the document also briefly touches upon massage applications, there is no teaching or suggestion as how the actuators' pressure profiles may be modified, adjusted or by other means be smoothed out to meet various medical criteria.

The published U.S. patent application No. 2003/0212306 discloses electroactive polymer-based artificial muscle patches to be implanted adjacent to a patient's heart. The document also describes artificial sphincters to be implanted around the urethra, the anal canal, or the lower esophagus. Thus, the solutions exclusively aim at body internal pressure applications. Naturally therefore, the pressure transition issues are quite different from any implementations wherein pressures are applied to the outside of the body. For example, inside the body, due to the absence of nerves the patient cannot normally feel discomfort. Instead, it is here more important to prevent tissue death and calous formation near the edges of the patches.

U.S. Pat. No. 6,123,681 describes a polymer stocking for applying compressive forces to inhibit the development of thrombophlebitis. Interestingly, this document does not address the way in which pressure application is smoothed out over the limb. Instead, it appears most likely that the proposed polymer strips, which are relatively far spaced from one another risk to cause pressure ulcers and tissue damages. Moreover, improper materials are selected for the intended application because none of the polymer strips are capable of providing the high forces required in the thrombophlebitis treatment.

SUMMARY OF THE INVENTION

The object of the present invention is therefore to alleviate the above-mentioned problems and thus accomplish improved pressure profiles in terms of a well-defined location, distribution and magnitude of the pressure that is applied to the outside a human body part.

According to one aspect of the invention, the object is achieved by the initially described device, wherein the device includes a pressure transition system, which is located relative to the body part, the first and second segments and has such mechanical properties that the pressure transition system is adapted to redistribute the basic pressure profiles between the first and second segments. The pressure redistribution is such that a control signal in respect of the first segment causes the pressure transition system to apply a first adjusted pressure profile to at least a part of the second portion of the body part, and correspondingly, a control signal in respect of the second segment causes the pressure transition system to apply a second adjusted pressure profile to at least a part of the first portion of the body part.

An important advantage attained thereby is that very flexible and well-controlled pressure profiles may be accomplished, which are adapted to suit the needs of various treatments. The proposed pressure transition system also facilitates pressure application in regions of the body not amendable to direct application from actuators, e.g. elbows and wrists. Thus, as a further consequence, patient mobility is facilitated during treatment. Also individual patient needs may be handled, such as in cases where the skin is extremely vulnerable. Since the pressure profiles associated with each segment are smoothed out, so that the patient senses relatively fuzzy pressures, the patient comfort during the treatment is generally enhanced. More important, however, the efficacy of the treatment is improved across joints and other complicated body regions where actuators cannot directly apply pressure.

According to one preferred embodiment of this aspect of the invention, a change of the actuator morphology is instigated by the electrical control signal. Moreover, each actuator is adapted to maintain a thus changed morphology on the basis of an electrical control signal which supplies charge replenishment to the actuator. Consequently, it is practically only necessary to add or remove charges when adjusting an actuator. The charge replenishment represents very small quantities of energy that compensate for charge leakage due to minor conductive effects in the electroactive-material. Since the altered morphology remains also after that the control signal ceased, the invention according to this embodiment is very power efficient, particularly with respect to static or quasi-static pressure profiles.

According to another preferred embodiment of this aspect of the invention, the pressure transition system is adapted to be positioned between the first and second segments when the device is fitted on the body part. This location of the pressure transition system is advantageous, since it enables pressure bridging between the segments. At the same time, the device may have a comparatively thin cross section.

According to yet another preferred embodiment of this aspect of the invention, the pressure transition system is adapted to be positioned between a first surface defined by the first and second segments and a second surface defined by the body part. The pressure transition system here extends over the first and second portions of the body part when the device is fitted on the body part. Consequently, a pressure profile generated by the first segment may efficiently "leak over" to the second portion of the body part via the pressure transition system, and vice versa.

Preferably the pressure transition system also has a low-friction surface towards the first and second segments. The surface is thereby adapted to allow a smooth tangential movement of the first and second segments relative to the pressure transition system. This design is advantageous because it mitigates any undesired effects on the body part, such as friction, caused by relative movements created by the segments' actuators.

According to still another preferred embodiment of this aspect of the invention, the first and second segments are arranged such that a portion of the first segment covers a portion of the second segment when the device is fitted on the body part. Thereby, an alternative, or complementary, means is provided for accomplishing a pressure profile leak-over between different segments and to attain smoothed-out/fuzzy pressure profiles.

According to another preferred embodiment of this aspect of the invention, the pressure transition system includes a number of collapsible ribs, which are adapted to extend along a general central axis of the body part. The ribs are positioned between at least one segment and a particular portion of the body part when the device is fitted on the body part. An actuator in each of the at least one segment is adapted to cause a tangential movement of the segment relative to the body part and the collapsible ribs are adapted to fold in response to this movement, such that when folded the ribs exert a radial pressure on the particular portion of the body part. Such a transformation between a tangential movement and a radial pressure is desirable because it allows a design with a very slim device profile.

Alternatively, or as a complement thereto, the pressure transition system may include at least one flexible chamber, which is adapted to be positioned between at least one of the segments and a particular portion of the body part when the device is fitted on the body part. An actuator in each of the at least one segment is adapted to cause a tangential movement of segment relative to the body part, and the at least one chamber is adapted to transform this movement into a resulting radial pressure on the particular portion of the body part.

According to yet another preferred embodiment of this aspect of the invention, the flexible chamber has an elastic wall of an anisotropic material, and the chamber is arranged relative to the body part when the device is fitted on the body part, such that the chamber is relatively stretchable in a circumferential direction of the body part and relatively stiff in a direction along a general central axis of the body part. Thus, any tension forces generated by the actuators may efficiently be transformed into desired pressure profiles with respect to the body part.

According to still another preferred embodiment of this aspect of the invention, the pressure transition system includes a number of protrusions adapted to be positioned between at least one of the segments and a particular portion of the body part when the device is fitted on the body part. The protrusions, in turn, are adapted to convert the basic pressure profile of the at least one segment into a non-uniform pressure profile to the particular portion of the body part. For example, the protrusions may be cylindrical bulges. However, the protrusions may also include at least one rigid rib, which is adapted to extend along a general central axis of the body part when the device is fitted on the body part. Then, as the segment exerts a pressure profile, a respective peak pressure ridge is defined by a positioning of each of the at least one rib relative to the body part. Consequently, an increased pressure can be attained at one or more desired areas.

According to yet another preferred embodiment of this aspect of the invention, the device includes a control unit adapted to produce a respective control signal to each of segment. The control unit is adapted to vary the control signal over time, so that a particular treatment profile is implemented with respect to the body part. Preferably, the treatment profile involves producing repeated cycles of variations between relatively high and relatively low basic pressure profiles by means of each segment. Hence, the device may perform an intermittent compression therapy and/or adjust (e.g. increase) the applied pressure gradually, and/or produce quasi-static pressure profiles.

According to still another preferred embodiment of this aspect of the invention, the pressure transition system includes a number of moisture passages adapted to receive exudates from the body part. Furthermore, the moisture passages (e.g. in the cells of an open-celled foam) may be adapted to transport (or milk) any received exudates from the body part to one or more liquid receptacles concomitantly with the repeating pressure cycles. Thereby, sweat can be removed from the patient's skin and exudates can be drawn from wounds.

According to another preferred embodiment of this aspect of the invention, the pressure transition system includes a number of air channels which are adapted to allow air to pass to the body part (e.g. via the cells of an open-celled foam). Preferably, also the air channels are adapted to exchange air between the body part and a local environment outside the device concomitantly with the repeating pressure cycles to improve the ventilation of the patient's skin.

According to yet another preferred embodiment of this aspect of the invention, the pressure transition system includes at least one sensor element adapted to register a physiological parameter of the body part. A data signal reflecting this parameter is transmitted to the control unit. Thereby, the control unit may survey and analyze the medical condition of the body part, and if necessary, trigger an alarm and/or alter the treatment profile.

According to still another preferred embodiment of this aspect of the invention, the pressure transition system includes at least one sensor element adapted to register a parameter expressing an environmental condition in proximity to the body part. A data signal reflecting this parameter is transmitted to the control unit. Thereby, the control unit may survey and analyze the environmental conditions for the body part, and if necessary, alter the treatment profile and/or trigger an alarm.

According to another preferred embodiment of this aspect of the invention, the pressure transition system includes at least one pocket adapted to contain a drug substance. The pressure transition system is also adapted to administer a transport of this substance to the body part. Thus, a pressure/massage treatment may be combined with a drug therapy. The drug substance may also be an antibacterial agent, so that the risk of infections and other sanitation related conditions could be reduced.

According to yet another preferred embodiment of this aspect of the invention, the drug substance is a gel adapted to perform a thermotherapy on the body part (i.e. either cryotherapy or heat therapy). Moreover, the gel may be adapted to facilitate activation of the actuator. Namely, if the actuator is of a conducting-polymer type, a gel-based electrolyte may both facilitate actuation of the actuator and accomplish the thermotherapy.

According to other preferred embodiments of this aspect of the invention, at least one of the actuators includes an electroactive material in the form of an electroactive polymer or ceramic, which is either a field activated electroactive material adapted to operate based on Maxwell stress effects, electrostrictive or piezoelectric effects, or an ionic electroactive material, for example a conducting polymer. Videlicet, due to their intrinsic characteristics, all these materials enable very compact and slim device designs that are suitable for many purposes, particularly within the medical field.

According to another aspect of the invention, the object is achieved by the initially described therapeutic garment, wherein the garment includes at least one of the proposed devices. Of course, such a garment is advantageous for the same reasons as the above-described device.

Hence, by means of the invention, a cost efficient solution is attained for applying an external pressure to a human body part, which also is highly flexible. The invention may be optimized for various medical purposes, and for instance be used for treatment or prophylaxis of lymphoedema, deep venous thrombosis, venous leg ulcers, venous insufficiency, arterial ulcers, arterial insufficiency, diabetic foot ulcers, cardiovascular diseases, claudication, burns and sports injuries. The proposed solution may also be used in stress therapy, massage therapy enhanced external counter pulsation therapy and blood pressure monitoring.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

FIGS. 1a-c show schematic cross-section views of devices according to embodiments of the invention, FIGS. 1d-e show schematic cross-section views of devices according to the prior-art solutions, FIGS. 4a-b show schematic cross-section views of a first embodiment of a proposed pressure transition system, FIGS. 5a-b show schematic cross-section views of a second embodiment of a proposed pressure transition system, FIGS. 6a-c show perspective views of further embodiments of the proposed pressure transition system, FIG. 7 shows a cross-section view of the pressure transition system according to a particular embodiment of the invention, FIGS. 8a-b illustrate a basic morphology of a planar field activated EAM-based actuator according to one embodiment of the invention, FIGS. 9a-c illustrate the morphology of a cylindrical field activated EAM-based actuator according to one embodiment of the invention, FIGS. 10a-b illustrate the morphology of a field activated EAM-based actuator of multilayer type according to one embodiment of the invention, FIGS. 17a-b illustrate the morphology of a triple ionic layer EAM-based actuator according to one embodiment of the invention, FIGS. 18a-c show side and top views of a conducting polymer actuator according to one embodiment of the invention, FIGS. 19a-b schematically illustrate the operation of a segment in a device according to one embodiment of the invention which includes actuators of the type shown in the FIGS. 18a-c, FIGS. 20a-b show side views of a bending actuator according to one embodiment of the invention, FIGS. 21a-b schematically illustrate the operation of a segment in a device according to one embodiment of the invention which includes actuators of the type shown in the FIGS. 16a-b, FIG. 22 schematically illustrates a devices according to one embodiment of the invention, and FIGS. 23-26 illustrate examples of therapeutic garments including the proposed device.

Figure 2:
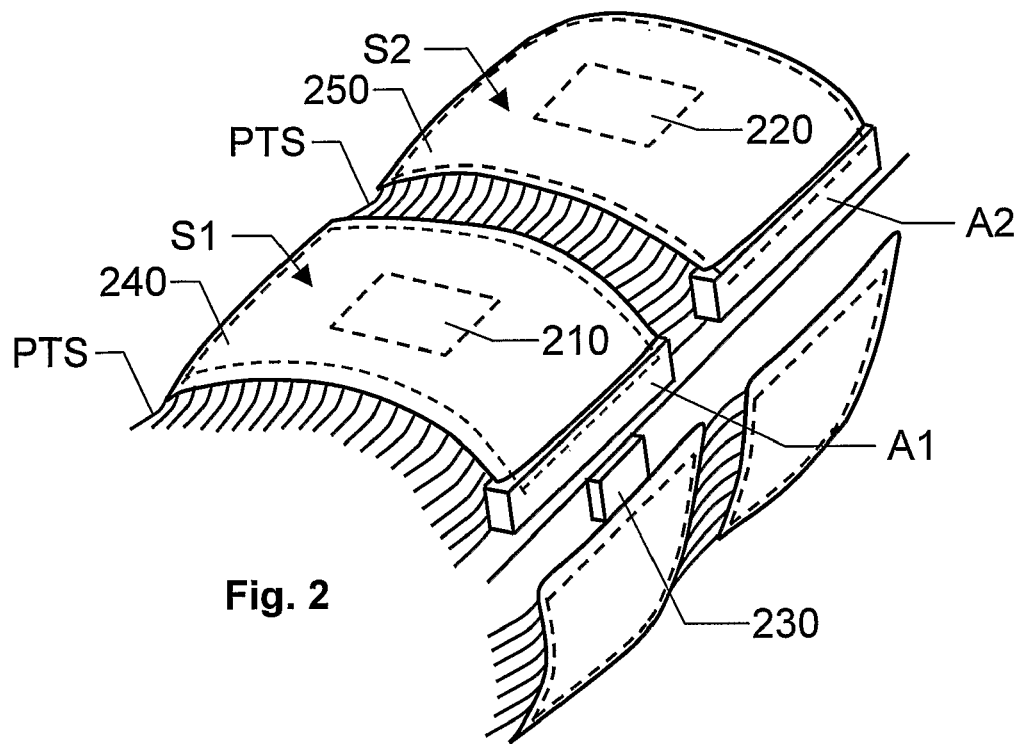
FIG. 2 shows a perspective view of a device according to a first embodiment of the invention.

DESCRIPTION OF PREFERRED
EMBODIMENTS OF THE INVENTION

FIG. 1a shows schematic cross-section view of a device according to one embodiment of the invention for exerting an external pressure to a human body part 100. The device includes a segment S1, which is adapted to at least partially enclose the body part 100 in a form-fitting manner. The segment S1 contains a controllable active-material based actuator A1 (e.g. of electroactive ceramics or polymer, conducting-polymer, carbon-nanotube or electroactive-gel type) that in response to a control signal is adapted to cause the segment S1 to apply a basic pressure profile P1 to the body part 100. A pressure transition system PTS of the device is adapted to redistribute this basic pressure profile P1 into an adjusted pressure profile $P1_{adj}$, which is different from the basic pressure profile P1. Thus, in response to a control signal in respect of the segment S1, the adjusted pressure profile $P1_{adj}$ is applied to the body part 100.

According to one embodiment of the invention, the pressure transition system PTS is an underlayer that is located between the segment S1 and the body part 100. Further, the pressure transition system PTS may include an auxetic-foam composite or alternative deformable microcellular structure, and have one or more walls of a stretchy fabric, which allow the system PTS to expand in the circumferential and/or axial directions, so that the external basic pressure profile P1 causes a deformation of the system PTS, and as a result an adjusted pressure profile $P1_{adj}$ is exerted on the body part 100.

The pressure transition system PTS may also include drug containing pockets (here generally illustrated by means of white circles). In this case, the system PTS is also adapted to administer a transport of any drug substance in these pockets to the body part 100, for instance in connection with an applied basic pressure profile P1. The drug substance may contain various topical agents for slow release application to the body part 100. Such topical agents may soften or moisturize the tissues in the body part 100 to prevent cracking and maintain or improve the overall health of the patient's skin. Alternatively, the drug substance may contain benzopyrones, flavonoids, coumarin, terpenses etc. for slow release into the underlying body part 100. Moreover, the drug substance may be an antibacterial agent, which helps in preventing infection of a wound site in the body part 100.

According to one embodiment of the invention, the drug substance is a gel, which is adapted to perform a thermotherapy on the body part 100 (e.g. a cryotherapy for pain relief, or a heat therapy to promote tissue healing). If the actuator A1 is based on an active material that requires an electrolyte and if a thermotherapy of the body part 100 is desired, it is preferable to let a gel based electrolyte play dual rolls in both operating the actuator A1 and accomplishing the cryotherapy.

FIG. 1b shows a schematic cross-section view of a device according to one embodiment of the invention where the device includes (at least) two segments S1 and S2. A first segment S1 at least partially encloses a first portion B1 of a body part 100 and a second segment S2 at least partially encloses a second portion B2 of the body part 100. The pressure transition system PTS is here adapted to redistribute pressure profiles between the first and second segments S1 and S2. Specifically, this means that if the first segment S1 receives a control signal which causes the segment S1 to generate a first basic pressure profile P1, the pressure transition system PTS applies a first adjusted pressure profile $P1_{adj}$ to at least a part of the second portion B2 of the body part 100. Correspondingly, if the second segment S2 receives a control signal which causes this segment S2 to generate a second basic pressure profile P2, the pressure transition system PTS applies a second adjusted pressure profile $P2_{adj}$ to at least a part of the first portion B1 of the body part 100. Hence, in response to control signals in respect of the segments S1 and S2 relatively smoothed-out, or fuzzy, pressure profiles are applied to the body part 100. This is advantageous both from a medical and a patient-comfort point-of-view.

According to one embodiment of the invention, the pressure transition system PTS is adapted to apply a bias pressure profile to the body part, such that the body part 100 is exerted to an initial pressure profile also before any of the basic pressure profiles P1 or P2 are applied. The bias pressure profile may be attained passively due to the pressure transition system PTS being stretchy. Then, the segments S1 and S2 may operate "on top of" this bias pressure profile to provide adjustments and/or dynamic therapies. Thereby, the pressure transition system PTS not only redistributes the basic pressure profiles P1 or P2 but also modifies the magnitude of the average pressure. For example, the segments S1 and S2 may apply basic pressure profiles P1 and P2 of 20 mmHg to the pressure transition system PTS, which already applies 20 mmHg to the body part 100. As a result, a pressure in the order of 40 mmHg is applied to the body part 100.

As can be seen in the FIG. 1$b$, at each body cross section enclosed by the device, the pressure transition system PTS is positioned between a first surface defined by the first and second segments S1 and S2, and a second surface defined by the body part 100. Additionally, the pressure transition system PTS extends over the first and second portions B1 and B2 of the body part 100.

In order to further illustrate the function of the proposed pressure transition system PTS we now refer to FIG. 1$c$. This figure shows a diagram wherein the horizontal axis indicates a position along the body part 100 and the vertical axis reflects a pressure towards the body part 100. A dashed line represents a desired pressure $P_{des}$ to be applied to the body part 100. As can be seen, the pressure transition system PTS a comparatively even pressure P approximately at the $P_{des}$-level along the entire extension of the pressure transition system PTS (i.e. also between and outside the segments S1 and S2).

FIGS. 1$d$ and 1$e$ illustrate a situation corresponding to that shown in the FIGS. 1$b$ and 1$c$, wherein the first and second segments S1 and S2 are form-fitted around the body part 100, however without any intermediate pressure transition system PTS. Here, unacceptable pressure peaks above the desired pressure $P_{des}$ occur at several places, particularly at the edges of the segments S1 and S2. The FIG. 1$e$ also illustrates separate pressure curves P1 and P2 respectively, which are caused by each individual segment S1 and S2 in the absence of the pressure transition system PTS.

FIG. 2 shows a perspective view of a device according to a first embodiment of the invention. Here, two segments S1 and S2 are shown. However, according to the invention, the device may include any number of segments larger than two. The pressure transition system PTS is at least positioned between the first and second segments S1 and S2. Thereby, the pressure transition system PTS may bridge over pressure profiles and tension forces from one segment to another, i.e. from S1 to S2, from S2 to S1, etc. Here, different degrees of coupling between the segments may be attained depending upon which fiber directions that are chosen for a fabric used in the pressure transition system PTS.

As mentioned above, according to the invention, each segment S1 and S2 includes an actuator A1 and A2 respectively. Here, the segments S1 and S2 include a respective strap member 240 and 250, and the actuators A1 and A2 are located at one end of each segment. The actuators A1 and A2 are further attached to the strap members 240 and 250, which at least partially enclose the body part 100. In response to control signals, the actuators A1 and A2 are adapted to pull the strap members 240 and 250, thus accomplish tension forces relative to the body part 100. According to the invention, many different forms of actuators may produce such tension forces. For example bending, spring, wrinkle, bellows, laminates, friction drives, linear stack piezoceramic (or c-block) and knitted fiber actuators may be used.

Nevertheless, in response to a respective control signal, the actuators A1 and A2 of FIG. 2 adjust their morphology so that a tangential movement T of segments S1 and/or S2 occurs. As a result, a radial pressure is exerted on the body part 100. For energy efficiency reasons, it is preferable that the actuators A1 and A2 be adapted to maintain their adjusted morphologies also after that the control signals have ceased, i.e. that the control signals merely instigate the morphology change.

According to a first alternative embodiment of the invention, the pressure transition system PTS is exclusively positioned between the segments S1 and S2. This design is preferable if a very slim device profile is important. However, according to a second alternative embodiment of the invention, the pressure transition system PTS also extends underneath the segments S1 and S2. In this case it is further preferable if the pressure transition system PTS has a low-friction surface towards the segments S1 and S2, so that smooth tangential movements of the segments' strap members are enabled.

According to this second alternative embodiment of the invention, the pressure transition system PTS may include sensor elements 210 and 220, which are adapted to register relevant parameters, and transmit data signals reflecting these parameters to a control unit for analysis.

For example, the sensor elements 210 and 220 may be adapted to register pressure, and in this case the elements can take the form of thin film force sensors (e.g. capacitive, piezoresistive, piezoelectric, varying contact or Quantum Tunneling Composite—QTC). If, on the other hand, the sensor elements 210 and 220 are intended to monitor the local circumference of the body part 100, the sensor element 230 may instead take the form of a resistive strip, an interdigitated electrode with contacts, or similar sensor which surrounds the body part 100. The sensor elements 210 and 220 may also be responsible for measuring physiological parameters, such as heart rate, galvanic skin response, electromyogram—EMG, blood oxygen levels, exudates extraction rates.

In the embodiment illustrated in FIG. 2, the pressure transition system PTS includes a sensor element 230 that is adapted to register a parameter expressing an environmental condition in proximity to the body part 100, e.g. temperature, airflow, humidity or contamination. Namely, these types of environmental conditions may also influence what is an ideal behavior of the proposed device. Thus, based on data signals from the sensor elements 210 and 220 and/or the sensor element 230, a treatment profile executed by the device may be adjusted.

Figure 3:
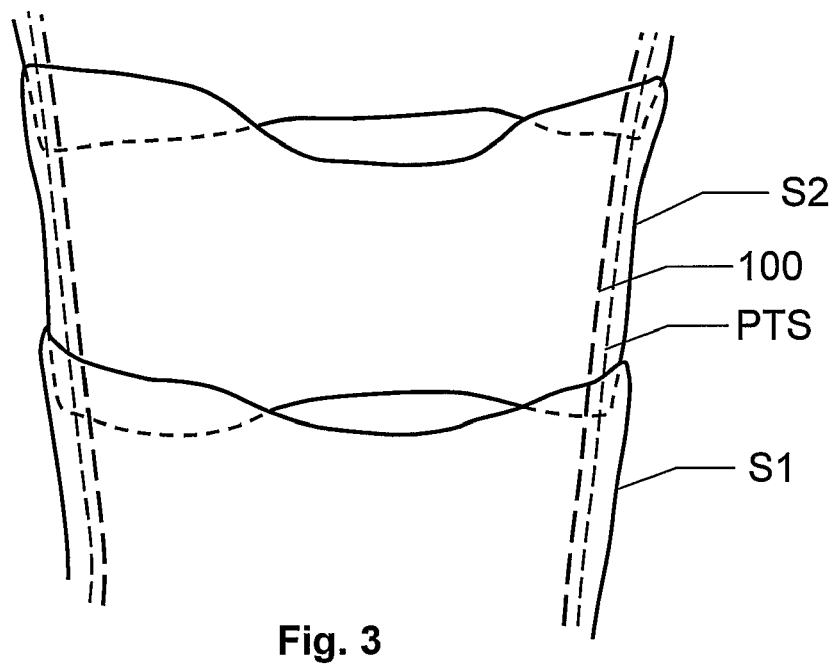
FIG. 3 shows a side view of a device according to a second embodiment of the invention.

FIG. 3 shows a perspective view of a device according to a second embodiment of the invention. Here, each of a number of segments S1, S2, etc. at least partially encloses a body part 100. Moreover, the segments are arranged such that a portion of one segment S1 covers a portion of a neighboring segment S2, and so on. Thereby, analogous to the embodiment described above with reference to FIG. 1b, relatively smoothed-out, or fuzzy, pressure profiles may be applied to the body part 100 in response to control signals in respect of the segments S1 and S2. Moreover, to redistribute these pressure profiles a pressure transition system PTS is located between the segments and the body part 100. Preferably, the pressure transition system PTS has a low-friction surface towards the segments S1 and S2, so that smooth tangential movements of the segments S1 and S2 are allowed relative to the pressure transition system PTS.

FIGS. 4a-b show two cross-section views of one embodiment of the proposed pressure transition system PTS.

Here, the pressure transition system PTS includes a number of collapsible ribs 410 which are positioned between at least one segment S1 and a particular portion of the body part 100 when the device is fitted on the body part 100. Preferably, a cover layer 420 separates the ribs 410 from the body part 100. The ribs 410 extend along a general central axis of the body part 100. Hence, in these cross-section views, we only see the section profile of the ribs 410. In response to a control signal, an actuator A1 of the segment S1 is adapted to cause a tangential movement T of the segment S1 relative to the body part 100 (see FIG. 4b). In response to the movement T, in turn, the ribs 410 are adapted to fold, such that when folded the ribs 410 exert a radial pressure P on the particular portion of the body part 100.

FIGS. 5a-b show two cross-section views of another embodiment of a proposed pressure transition system PTS. Also in this case, the pressure transition system PTS is adapted to trans-form a tangential movement T into a resulting radial pressure P on a body part 100. Here, however, the pressure transition system PTS includes at least one flexible chamber 510, which is positioned between at least one segment S1 and the body part 100 when the device is fitted on the body part 100. An actuator A1 of the segment S1 is adapted to cause the tangential movement T of the segment S1 relative to the body part 100 in response to a control signal. The tangential movement T, in turn, deforms the flexible chamber 510, so that the chamber 530 causes a radial pressure P on the body part 100, preferably via an underlayer 520. The chamber 510 has at least one attachment point 530 to the segment S1. When the segment S1 slides over the body part 100 the attachment point 530 follows this movement, and the chamber 510 is compressed. The chamber 510 may contain any flexible medium, such as a gas, a gel or a liquid. In any case, chamber 510 has elastic walls, which according to a preferred embodiment of the invention are made of an anisotropic material. Thereby, the chamber 510 may be arranged relative to the body part 100 when the device is fitted thereto, such that the chamber 510 is relatively stretchable in a circumferential direction of the body part 100 and relatively stiff in a direction along a general central axis of the body part 100. Thus, the radial pressure P may be well distributed over the body part 100. At the same time, the pressure transition system PTS can be soft in the circumferential direction, so that fit and patient comfort is enhanced.

Generally, the tension-force to pressure transduction embodiments illustrated in the FIGS. 4a-b and 5a-b may provide useful designs whenever a slim, robust and energy efficient device is desired.

FIG. 6a shows a perspective view of another embodiment of the proposed pressure transition system PTS, which includes a number of protrusions in the form of rigid ribs 620. These ribs 620 are adapted to be positioned between at least one segment S1, S2 and S3 respectively and a particular portion of the body part 100. The ribs 620 are adapted to extend along a general central axis of the body part 100 and to convert the basic pressure profile of the segments S1, S2 and S3 into a non-uniform pressure profile to the particular portion of the body part 100. Thus, a peak pressure ridge of the non-uniform pressure profile is produced for each rib, and the pressure ridges are defined by the positioning of the ribs 620 relative to the body part 100. More important, however, by means of the ribs 620 pressure profiles applied by the segments S1, S2 and S3 are distributed across the body part 100. Preferably, the ribs 620 may be sewn into a soft backing material, so that the entire structure can easily expand in the radial direction (e.g. to accommodate a wide range of patient limb sizes) while being stiff in the axial direction (i.e. along the body part 100). For illustrative purposes, the segments S1, S2 and S3 have here been separated more than what is normally preferable.

FIG. 6b shows a perspective view of an alternative embodiment of the proposed pressure transition system PTS, where instead the protrusions are cylindrical bulges 630. The bulges 630 are adapted to be positioned between at least one segment S1 and a particular portion of the body part when the device is fitted on the body part. Analogous to the above-mentioned ribs, the bulges 630 are adapted to convert the basic pressure profile of the segment S1 into a non-uniform pressure profile to the particular portion of the body part. Here, however, each bulge 630 causes a circular pressure peak. Such pressure peaks are particularly suitable when treating lymphoedema.

FIG. 6c shows yet another perspective view of a device according to one embodiment of the invention. The device includes a number of segments S1, S2, . . . , Sn, which are arranged linearly along a body part 100, such as an arm or a leg. Analogous to the embodiment shown in FIG. 6a, for illustrative purposes, the segments S1, S2 and S3 have also here been separated more than what is normally preferable. Nevertheless, each segment S1, S2, . . . , Sn is associated with a pressure transition system PTS which encloses the body part 100 and has fiber directions according to the curved lines. Moreover, the pressure transition systems PTS overlap partially, such that some portions of the body part 100 are covered by more than one pressure transition system PTS. For instance, a majority of the body part 100 may be covered by at least two different pressure transition systems PTS. This configuration results in that an activation of a first segment S1 causes a pressure to be applied to portions of the body part 100 which may also be pressurized via a second segment S2, and so on. Hence, smoothed-out, or fuzzy, pressure profiles may be applied to the body part 100 in response to control signals C(i) in respect of the segments S1, S2, . . . , Sn.

According to a preferred embodiment of the invention, a control unit 640 produces a respective control signal C(i) to each of segment S1, S2, . . . , Sn. Preferably, these control signals C(i) are distributed via a common signal delivery system 650. The control unit 640 is adapted to vary the control signals C(i) over time, so that a treatment profile is implemented with respect to the body part 100. The treatment profile may involve producing repeated cycles of variations between relatively high and relatively low basic pressure profiles by means of each segment S1, S2, . . . , Sn.

The treatment profile, in turn, may be adaptive in response to a manipulation signal that either is an external signal, or is produced by the device itself. For example, as mentioned above with reference to the FIG. 2, one or more sensor elements in the segments S1, S2, ..., Sn may transmit data signals R to the control unit 640. Consequently, the manipulation signal can be based on such data signals R, so that the treatment profile depends on a current state of the body part 100 and/or the current environmental conditions. Moreover, the data signals R may reflect a patient's posture. Therefore, according to the invention, it is rendered possible to adapt the treatment profile to the posture. For example, if the segments S1, S2, ..., Sn are fitted around the patient's leg, they may be completely relaxed when the patient is lying down (e.g. apply a pressure profile in the range 0-10 mmHg), apply a relatively low graduated pressure profile (e.g. in the range 0-40 mmHg) when the patient is standing up and apply a relatively high graduated pressure profile (e.g. in the range 0-60 mmHg) when the patient is sitting.

According to preferred embodiment of the invention, the control signals C(i) are electrical signals, and the segments S1, S2, ..., Sn have actuators whose morphology is electrically adjustable. Moreover, the adjustments of the actuator morphologies are preferably only instigated by the control signals C(i) (i.e. no control signal is necessary to maintain an adjusted morphology).

Naturally, according to the invention, the control unit 640 may be connected to any of the proposed segments and pressure transition systems, i.e. not only the elements of embodiment shown in FIG. 6c.

FIG. 7 shows a cross-section view of the pressure transition system PTS according to one embodiment of the invention, where the pressure transition system PTS includes a number of moisture passages 710 schematically illustrated as tubes with internal flanges. Each moisture passage 710 is adapted to receive exudates from the body part 100, and thus assist in keeping the skin relatively dry.

According to one preferred embodiment of the invention, the pressure transition system PTS includes one or more liquid receptacles 715, and the moisture passages 710 are adapted to transport any received exudates from the body part 100 this/these receptacle/s 715 concomitantly with repeating cycles of a treatment profile executed by means of segments S1 and S2 associated with the pressure transition system PTS. Preferably, the moisture passages 710 and liquid receptacles 715 are accomplished by means of air pockets of an open-celled foam. Thus, these elements' physical configuration is quite dissimilar from what is illustrated in FIG. 7, however their function is identical thereto.

According to another preferred embodiment of the invention, the pressure transition system PTS includes a number of air channels 720 which are adapted to allow air to pass to the body part 100. Analogous with the moisture passages 710 and the liquid receptacles 715, the air channels 720 may also be adapted to operate concomitantly with the repeating cycles of the treatment profile executed by means of the segments S1 and S2, so that air is exchanged more efficiently between the body part 100 and a local environment outside thereof. Moreover, open-celled foam openings may also constitute the air channels 720.

FIG. 8a illustrates the basic morphology of a planar field activated EAM-based actuator 805. Two essentially plate-shaped electrodes 810 and 811 are here separated by means of an EAM piece 820. When an electric field is applied over the EAM piece 820, i.e. when one of the electrodes 810 is connected to a first polarity, say a positive voltage, and the other electrode 820 is connected to a second polarity, say a negative voltage, the EAM piece 820 undergoes a shape change, for instance by becoming thinner and longer. This situation is shown in FIG. 1b.

The shape change of the EAM 820 arises due to a variety of physical reasons when a non-zero charge is supplied to the electrodes 810 and 811, for example via a power supply or a control signal. In response to such a charge, the EAM 820 attempts to undergo a change in shape. The magnitude of the shape change depends on the material properties of the EAM 820, the frequency of the charge application/removal and mechanical boundary conditions of the material. Typically, the change in shape is related to the amount of charge accumulated on the surrounding electrodes 810 and 811.

In all dielectric materials, charge accumulation on adjacent electrodes creates mechanical stress in the material due to attraction and repulsion of the adjacent charges. Such stresses are referred to as Maxwell stresses. In soft materials, e.g. dielectric elastomers and gels, these stresses are sufficient to cause a significant shape change of the material.

Also in crystallographic materials, such as ceramics and ferroelectric polymers, an appreciable change in properties occurs with shape change of the material. This phenomenon is referred to electrostriction. Due to electrostrictive effects, the material will strive at changing the shape in response to an applied charge (in addition to Maxwell stress effects). Furthermore, an initial polarization may be frozen into some EAMs during manufacture. In materials capable of maintaining an initial polarization, the applied charge elicits a change in shape referred to as the reverse piezoelectric effect. Piezoelectric effects generally demonstrate a linear relationship between material strain and resulting electric field. Electrostrictive effects, on the other hand, generally demonstrate a quadratic relationship between material strain and applied electric field under linear boundary conditions. Under certain circumstances, these effects are reversible. Therefore, when the electroactive material undergoes a shape change, an electrical response occurs. This allows electric energy to be captured from the moving electroactive material. It also enables for the materials to operate as sensors.

Another important property of the EAMs is that a deformation (i.e. a changed morphology) resulting from an applied charge will be maintained if the electrodes are left open-circuited. Nevertheless, due to slight conductive effects, the thus separated charges will slowly leak through the EAM. Therefore, in practice, some replenishment/maintenance charge is necessary to top up the existing charge, and maintain a desired deformation.

FIGS. 9a and 9b illustrate top- and side views respectively of the morphology of a cylindrical field activated EAM-based actuator 905, which may be used to apply pressure according to the invention. Here, a first cylindrical electrode 910 is enclosed by an EAM piece 920. A second electrode 911, in turn, encloses the EAM piece 920. FIG. 9c shows a side-view corresponding to the FIG. 9b, however where the first electrode 910 is connected to a positive voltage and the second electrode 911 is connected to a negative voltage. In similarity with the example shown in FIG. 8b, the EAM piece 920 contracts in response to the applied electric field, and the actuator's 905 diameter decreases while its length increases.

A multilayer cylindrical actuator of the type shown in the FIGS. 9a and 9b may be accomplished straightforwardly by wrapping a planar actuator around a spring, or tube-like mandrel. Thereby, a compact, multilayered (i.e. high strength) tubular actuator can be cost effectively created from a simple planar starting geometry.

FIG. 10a shows a schematic side-view of a field activated EAM-based actuator 1005 of multilayer (or stacked) type, which may be used according to the present invention. Many interconnected layers of EAM 1020 are here alternately separated by a first essentially planar electrode 1010 and a second essentially planar electrode 1011. FIG. 10*b* illustrates the case when an electric field is applied across the electrodes 1010 and 1011. As can be seen, this again results in a contraction of the EAM 1020. However, a material expansion may instead result if for example a piezoceramic is used as the EAM 1020. In any case, by means of a stacked-type of actuator, a substantial mechanical amplification can be achieved. Triple layer actuators (or so-called bimorph cantilever actuators) can be formed by means of two EAM pieces separated by a supporting element, where opposite electric fields are applied to the EAM pieces. Thereby, the actuator can be controlled to bend in two different directions depending on which EAM piece that is activated, or the polarities applied to each of the EAM pieces.

Moreover, according to the invention, layers of passive materials may also be laminated along with the active material. These extra layers are often useful when interfacing with the surroundings, improving adhesion between adjacent active material layers, and creating favorable residual stresses in the active material during manufacturing.

Figure 11A:
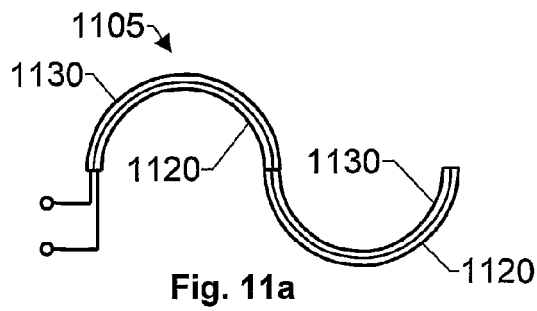
FIGS. 11a-b illustrate the morphology of a field activated EAM-based actuator of C-block type according to one embodiment of the invention.
Figure 11B:
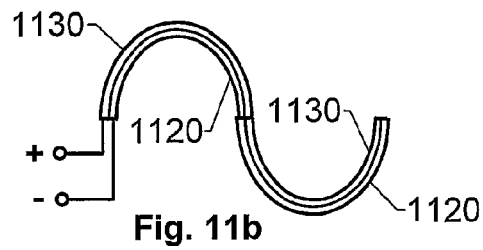

FIG. 11*a* shows a schematic side view of a field activated EAM-based actuator 1105 of C-block type, which also may be used according to the invention. In each block of this actuator 1105 a curved-profile laminate material 1130 adjoins an EAM piece 1120, which likewise has a curved profile. The general curved profile of each block amplifies the motion of the basic movement of the EAM piece 1120. Two or more of these blocks may be connected in series with one another to accomplish a further amplification effect. When an electric field is applied between the respective EAM piece 1120 and the laminate material 1130, the EAM piece 1120 contracts according to what is illustrated in FIG. 11*b*.

Figure 12A:
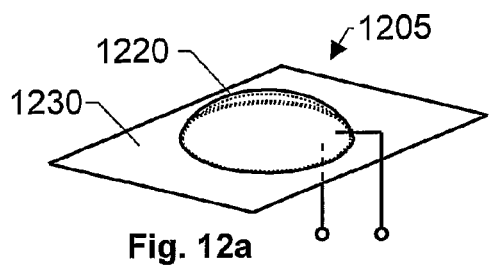
FIGS. 12a-b illustrate the morphology of a field activated EAM-based actuator of bubble type according to one embodiment of the invention.
Figure 12B:
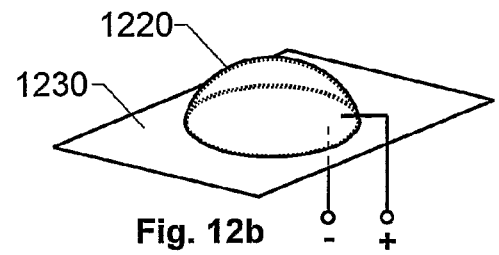

FIG. 12*a* illustrates the morphology of a field activated EAM-based actuator 1205 of bubble type according to one embodiment of the invention. Here, an EAP membrane 1220, shaped as a truncated sphere (or similar bubble-like shape), is attached to a rigid mounting material 1230. According to one embodiment of the invention, a pneumatic pressure bias is used to create the convex shape of the EAP membrane 1220. An electric field across the EAP membrane 1220 causes the membrane 1220 to expand from its initial (inactivated) morphology. FIG. 12*b* illustrates such an activated state. For example, such actuators can be used to create localized pressure points on the body.

Figure 13:
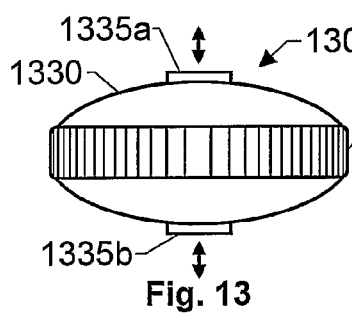
FIG. 13 shows a field activated EAM-based actuator of a first cymbal type according to one embodiment of the invention.

FIG. 13 shows a field activated EAM-based actuator 1305 of cymbal type according to one embodiment of the invention. Multilayered EAM strips 1320 are here located between two flexible, cymbal-shaped interface elements 630. When activated, i.e. in response to an electric field across the EAM strips 1320, the strips 1320 contract or expand and pull/push the interface elements 1330 inwards or outwards as indicated by the arrows. Thereby, a pressure can be applied via first and second contact surfaces 1335*a* and 1335*b* respectively, which are located at the distal ends of the interface elements 1330. Preferably, the interface elements 1330 are flexible and the EAM strips 1320 are oriented with their longest sides parallel to a symmetry axis of the interface elements 1330, i.e. according to a layered structure as illustrated in the FIG. 13.

Figure 14A:
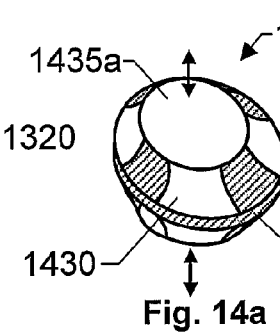
FIGS. 14a-b show a field activated EAM-based actuator of a second cymbal type having a flexible interface to link mechanical energy produced the actuator towards a body part according to one embodiment of the invention.
Figure 14B:
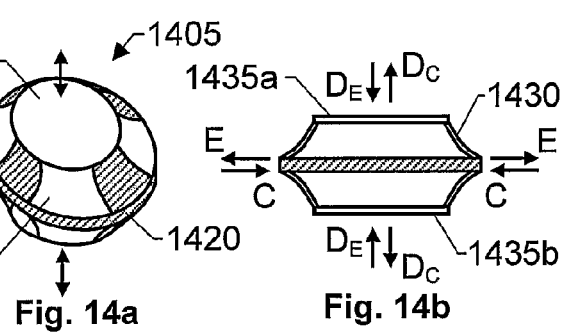

FIG. 14*a* shows a perspective view of another cymbal type of field activated EAM-based actuator 1405, which may be used in a device according to the invention. FIG. 14*b* shows a sectional side view of this actuator 1405. Here, two interface surfaces 1435*a* and 1435*b* are interconnected by means of a number of flexible members 1430, which in turn, are attached to an EAM piece 1420 located between the interface surfaces 1435*a* and 1435*b*. Thereby, upon activation of the actuator 1405, so that the EAM piece 1420 expands E, the interface surfaces 1435*a* and 1435*b* move toward one another $D_E$ (essentially along their symmetry axes). Analogous thereto, upon activation of the actuator 1405, so that the EAM piece 1420 instead contracts C, the interface surfaces 1435*a* and 1435*b* are separated from one another $D_C$ (essentially along their symmetry axes). Hence, a desired pressure can be created towards a body part through transformation of the basic material movement of the EAM piece 1420.

Figure 15A:
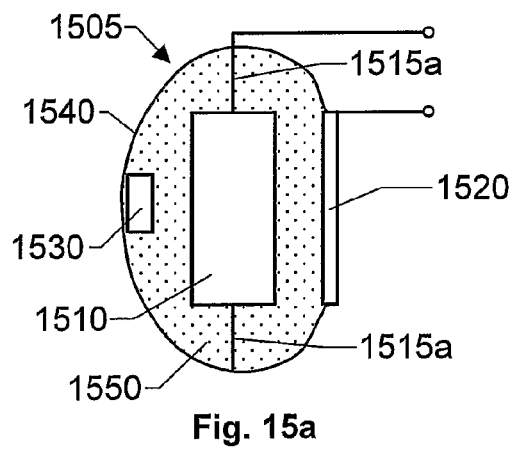
FIGS. 15a-b illustrate a basic morphology of an ionic EAM-based actuator according to one embodiment of the invention.

FIG. 15*a* illustrates a basic morphology of an ionic EAM-based actuator 1505 according to one embodiment of the invention. Ionic electroactive materials are characterized in that actuator systems based on them contain ions and that migration of these ions occurs under the influence of voltage potentials applied between electrodes 1510 and 1520 within the system. The ion migration, in turn, causes swelling or shrinking of the actuator. There are many designs based on the concept of electrically induced ionic migration. Some exemplary designs, which may be used according to the invention will be discussed below with reference to FIGS. 16 to 17.

In similarity with field activated EAMs, ionic electroactive material reactions are reversible. Therefore, actuators based on ionic EAMs can also be used as various types of sensors and energy accumulators.

Returning now to FIG. 15*a*, conducting polymer actuators generally have an ion reservoir, such as an electrolyte 1550 (in the form of a liquid, a gel or a solid), which separates a working electrode 1510 and a counter electrode 1520. The working electrode 1510 usually includes the EAM (i.e. the conducting polymer). Also the counter electrode 1520 may include an EAM, however usually different from the EAM of the working electrode 1510. The counter electrode 1520 may thus include a naturally conducting material, such as a metal or a graphite film. Moreover, the counter electrode 1520 may be made from nanocomposites, fabricated to have both high conductivity and low mechanical stiffness.

The working electrode 1510 may likewise include a composite of active materials and passive materials. In such cases, the passive materials are normally included to improve the conductive properties of the working electrode 1510 while not impeding movement of the electrode during operation. Also here, conductive nanocomposites represent a viable option for lamination with the conducting polymer material.

In some cases, a reference electrode 1530 is present in the electrolyte 1550 to ensure that desired voltage potentials are maintained at appropriate levels at the other electrodes 1510 and 1520 during operation of the actuator 1505. When the voltage potentials of the electrodes 1510 and 1520 are varied, the electroactive polymer can undergo oxidation or reduction reactions. Large electric fields are generated at the interfaces between the electrodes 1510 and 1520 respectively and the electrolyte 1550. This causes ion migration across the interfaces. Ions within the EAM can initiate conformational change of the crystallographic structures of the material, or they may take up interstitial spaces in the material and cause it to swell. If ions are extracted from the EAM in the working electrode 1510 due to migration, the working electrode 1510 may shrink. Depending on the counter electrode material, reactions at the electrode 1520 may or may not result in another usable shape change in respect of this electrode. The details of the entire actuator system (such as the specific EAMs, electrolyte and counter electrode properties) together dictate the final response of the system during operation.

Figure 15B:
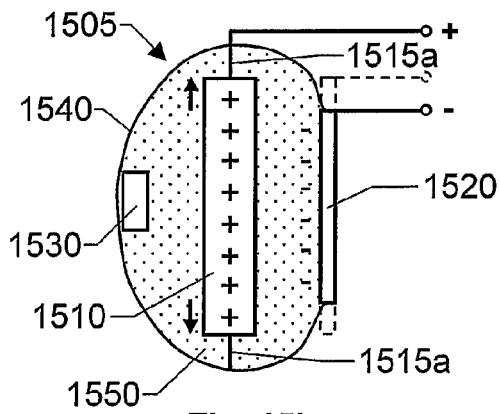

FIG. 15*b* illustrates a situation where a positive voltage has been applied to the working electrode 1510 and a negative voltage has been applied to the counter electrode 1520. As a result, the working electrode 1510 extends while its width decreases. For improved expansion properties, the working electrode 1510 may be designed as a composite of conductive helical supporting structure encapsulated by the EAM (not shown here). A possible extension of the counter electrode 1520 (resulting from an included EAM) is illustrated by means of a dashed profile.

In the case of carbon nanotubes, the presence of carbon nanotubes dramatically increases the surface area of the electrode. This, in turn, increases the strength of the electromagnetic field during a reduction or oxidation process. Consequently, an increased ion migration occurs and therefore an amplified mechanical response can be obtained. The formation of gas can arise intimately with the electrode during a reaction (often due to electrolysis of water). Of course, the expansion of such gases may also result in an increased response.

Figure 16A:
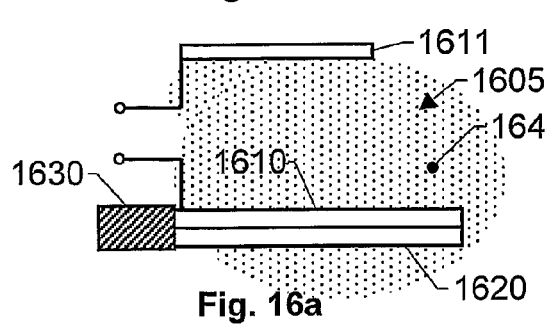
FIGS. 16a-b illustrate the morphology of a bilayer ionic EAM-based actuator according to one embodiment of the invention.
Figure 16B:
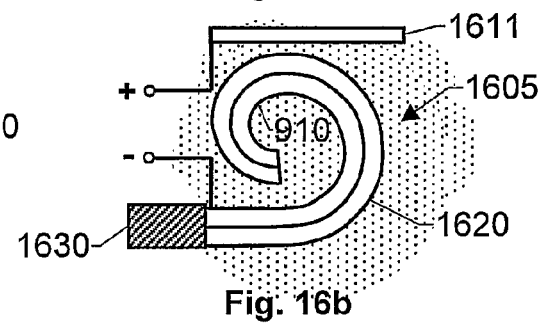

FIG. 16*a* illustrates the morphology of a bilayer ionic EAM-based actuator 1605 according to one embodiment of the invention. Here, a working electrode 1610 of a conductive polymer (EAP) adjoins a non-conducting polymer backing element 1620, which mainly functions as a mechanical support to the actuator laminate of the working electrode 1610. A counter electrode 1611 is arranged physically separated from both the working electrode 1610 and the backing element 1620. The working electrode 1610 and the EAP 1620 are attached to an anchor member 1630, and all the elements 1610, 1620 and 1611 are surrounded by an electrolyte 1640. FIG. 16*b* shows a situation when a negative voltage has been applied to the working electrode 1610 and a positive voltage has been applied to the counter electrode 1611, causing the conductive polymer to contract, and as a result, the entire working electrode and backing element system to bend.

FIG. 17*a* illustrates the morphology of a triple ionic layer EAM-based actuator 1705 according to one embodiment of the invention, which is similar in morphology to the actuator design of FIGS. 16*a* and 16*b*. Here however, two conductive polymer electrodes 1710 and 1711 are separated by means of a non-conducting polymer element 1720. All the elements 1710, 1711 and 1720 are attached to an anchor member 1730, and may or may not be surrounded by an electrolyte. Namely, the non-conducting polymer element 1720 may include a solid polymer electrolyte, and thus forego the need for a surrounding electrolyte. In such a case, the elements 1710, 1711 and 1720 must be encapsulated to prevent evaporation of the electrolyte. FIG. 17*b* illustrates how the actuator 1705 upon activation can be controlled to flex in different directions $\Sigma_1$ and $\Sigma_2$ depending on the polarity of a voltage applied between the electrodes 1710 and 1711. In this case, the actuator 1705 bends upwards $\Sigma_1$ in response to a negative voltage potential connected to the first electrode 1710 and a positive voltage potential connected to the second electrode 1711. Correspondingly, the actuator 1705 would bend downwards $\Sigma_2$ in response to opposite voltage potentials.

In addition to the actuator morphologies shown in the FIGS. 15 to 17, the actuators according to the invention may take the form of fibers, fabrics or strips based on the basic concept ionic EAM-based actuators. Naturally, according to the invention, the basic actuator morphologies may be combined and be arranged in arrays to produce more advanced actuators.

FIG. 18*a* shows a side view of an inactivated conducting polymer actuator A1 according to one embodiment of the invention. FIG. 18*b* shows a corresponding top view. This actuator A1 operates according to the basic principle described above with reference to the FIGS. 15*a* and 15*b*. Nevertheless, both a working electrode 1810 and a counter electrode 1820 include a conductive polymer. An electrolyte 1830 is enclosed by these electrodes 1810 and 1820. The actuator A1 is activated by means of an applied voltage between a first electrode tab 1810*a* and a second electrode tab 1810*b*. When such a voltage is applied, the working electrode 1810 contracts and the counter electrode 1820 expands. As a result, the actuator A1 both contracts in plane and expands out of the plane according to the top-view illustration of FIG. 18*c*.

FIG. 19*a* illustrates a side view of a segment in a device according to one embodiment of the invention, which includes a number of actuators $A1_1$, $A1_2$, and $A1_3$ of the type shown in the FIGS. 18*a-c*. Theoretically, one actuator is sufficient to exert an external pressure to a body part 100 by means of the proposed device. However, for improved effect a plurality of actuators may be used. If so, the actuators are mechanically connected to one another to at least partially enclose the body part 100, such as the limb of a patient, in a form-fitting manner. Depending on the number of actuators and the range of motion of each actuator $A1_1$, $A1_2$ and $A1_3$, the device may be capable of completely disengaging the body part 100 at the conclusion of treatment. In this case, a strap 1910 (or equivalent) transmits actuator forces around the body part 100 and fixates the actuators $A1_1$, $A1_2$ and $A1_3$ to the body part 100. In other cases, the strap 1910 may contain a variety of locking mechanisms to assist with the removal of the device from the patient after treatment, or assist with size adjustment of the device to the patient.

Here, a first actuator $A1_1$ includes a first working electrode $1810_1$ and a first counter electrode $1820_1$; a second actuator $A1_2$ includes a second working electrode $1810_2$ and a second counter electrode $1820_2$; and a third actuator $A1_3$ includes a third working electrode $1810_3$ and a third counter electrode $1820_3$. Further, the first actuator $A1_1$ is connected to the second actuator $A1_2$, which in turn, is connected to the third actuator $A1_2$ according to the configuration of FIG. 19*a*. Strap members 1910 are attached to the first and third actuator $A1_1$ and $A1_3$ to fixate the device to the body part 100. The electrode tabs of each actuator $A1_1$, $A1_2$, and $A1_3$ are also electrically connected to an electric power source, so that the actuators can be activated by means of electric charges being supplied to their electrodes. However, for reasons of a clear presentation, this is not shown in the FIG. 19*a*.

Preferably, a pressure transition system PTS is arranged as an interface between the actuators $A1_1$, $A1_2$ and $A1_3$ and the body part 100. The pressure transition system PTS is adapted to re-distribute a basic pressure profile of the actuators $A1_1$, $A1_2$ and $A1_3$, such that when the actuators are activated, an adjusted pressure profile different from the basic pressure profile is applied to the body part 100. Thereby, a smoother (or more fuzzy) pressure profile P can be applied to the body part, which is desirable in many medical applications.

According to another preferred embodiment of the invention, any voids between the actuators $A1_1$, $A1_2$ and $A1_3$ and the pressure transition system PTS are filled with an open-celled foam (not shown). Namely, this further assists in redistributing pressure from the actuators $A1_1$, $A1_2$ and $A1_3$ to the body part 100 without overly affecting the breath ability of the device.

FIG. 19*b* illustrates a situation when all the actuators $A1_1$, $A1_2$ and $A1_3$ are activated, and therefore each actuator $A1_1$, $A1_2$ and $A1_3$ has adapted morphology equivalent to what is shown in the FIG. 18*c*. As a result, a pressure profile P is applied to the body part 100, and as a further consequence the body part 100 is normally compressed/deformed (which is here illustrated by means of a reduced cross-section diameter). If, however, the body part 100 were very stiff, and therefore would not deform under the pressure profile P applied, the actuators $A1_1$, $A1_2$ and $A1_3$ and the strap members 1910 would exert tensile forces F around the body part 100 without undergoing the large deformations depicted in the FIG. 19*b*.

Figure 20A:
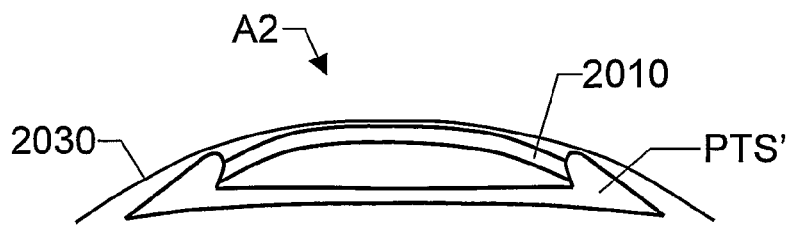
Figure 20B:
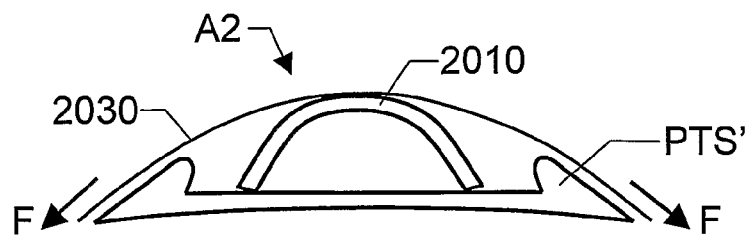

FIGS. 20*a* and 20*b* show side views of a bending actuator A2 according to one embodiment of the invention. Preferably, this type of actuator A2 includes a bending member 2010 of field activated EAM-type. The bending member 2010 is adapted to operate against a local pressure transition system PTS' and an over layer 2030, for instance in the form of an appropriate interfacing fabric. An elastic back plate side of the bending member 2010 faces the over layer 2030. FIG. 20*a* illustrates an inactivated state of the actuator A2, while FIG. 20*b* illustrates an activated state. As can be seen, when activated the bending member 2010 pushes the over layer 2030 away from the local pressure transition system PTS'. This leads to tensile forces F in the over layer 2030, which according to the invention may be converted into a desired pressure profile applied to a body part.

Figure 21A:
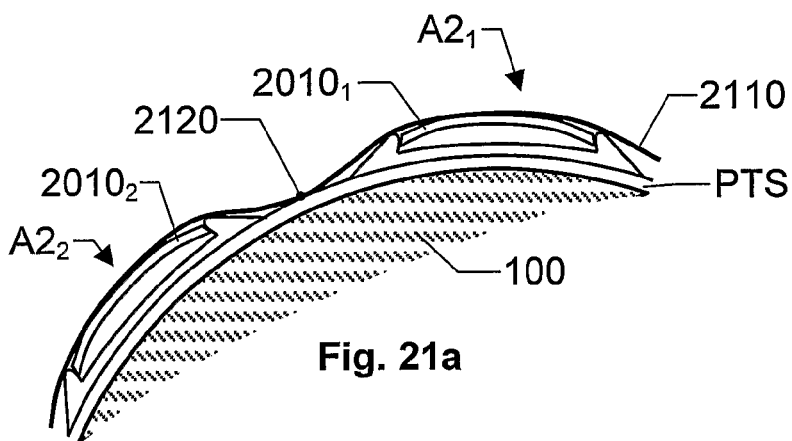

FIG. 21*a* shows a side view of a segment in a device according to one embodiment of the invention, which includes a number of actuators A$2_1$ and A$2_2$ of the type shown in the FIGS. 20*a* and 20*b*. In the configuration shown, the number of actuators is increased to accommodate a wider range of available motion, and to more evenly distribute pressure to a curved body part 100. If an increase pressure is desired, two or more actuators may be applied in parallel, i.e. be stacked, such that the actuators a layered on top of one another. Alternatively, multilayered laminates within each actuator element of an actuator array may be thickened. Nevertheless, for illustrative purposes only two actuators A$2_1$ and A$2_2$ are shown here. The actuators A$2_1$ and A$2_2$ are located next to one another and have a common over layer 2110 (compare with 2030 in the FIGS. 20*a* and 20*b*). Preferably, the over layer 2110 has at least one attachment point 2120 between the actuators A$2_1$ and A$2_2$. Thereby, when activated, each actuator A$2_1$ and A$2_2$ contributes maximally to the generation of a pressure towards the body part 100. Moreover, in addition to the local systems of each actuator, a pressure transition system PTS is preferably arranged as an interface between the actuators A$1_1$ and A$1_2$ respectively and the body part 100. Such a pressure transition system PTS is adapted to redistribute a basic pressure profile of the actuators A$1_1$ and A$1_2$, so that when the actuators are activated, an adjusted pressure profile different from the basic pressure profile is applied to the body part 100. Thereby, a smoother (or more fuzzy) pressure profile P can be applied to the body part, which is desirable in many medical applications.

Figure 21B:
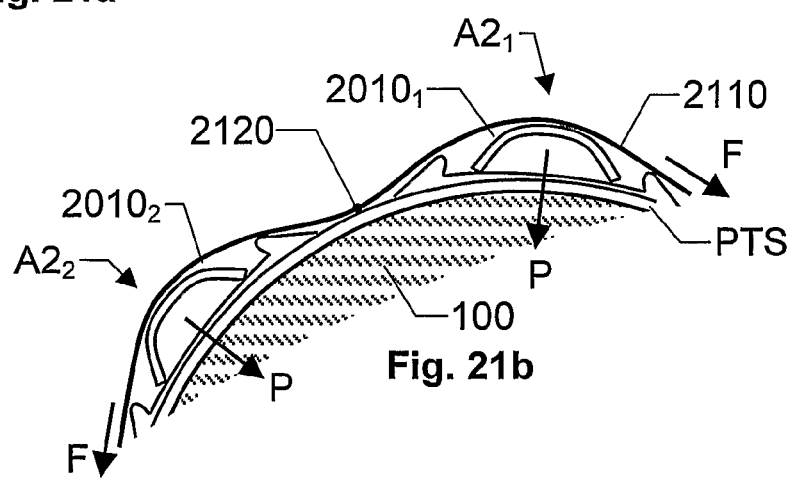

In similarity with the FIG. 19*b*, FIG. 21*b* shows a situation when the actuators A$1_1$ and A$1_2$ are activated, and a pressure profile P is applied to the body part 100. Normally, this leads to a compression/deformation of the body part 100 (which is here illustrated by means of a reduced cross-section diameter). If, however, the body part 100 were very stiff, and therefore would not deform under the pressure profile P applied, yet the over layer 2110 would still exert tensile forces F around the body part 100.

For proper function, the outer layer 2110 should be made of a rigid and strong fabric, so that it does not stretch appreciably during activation of the actuators A$2_1$ and A$2_2$. Therefore, the outer layer 2110 is preferably a knitted anisotropic material, which includes fibers (e.g. of Kevlar) that are strong in the circumferential direction (i.e. around the body part 100), and relatively soft in the axial direction (i.e. along the body part 100). Moreover, the outer layer 2110 fabric preferably has an open weave to ensure that the breath ability of the device is not compromised.

FIG. 22 shows a side view of a device according to one embodiment of the invention for exerting an external pressure to a human body part 100. The device includes segments S1, S2 and S3, which are adapted to at least partially enclose the body part 100 in a form-fitting manner. Each segment S1, S2 and S3 contains a controllable active-material based actuator A (e.g. of the type illustrated in the FIGS. 21*a* and 21*b*) that is adapted to cause the segment to apply a pressure profile to the body part 100 in response to a control signal C(i). The device may also include a pressure transition system PSS, which is adapted to re-distribute a basic pressure profile produced by the segments S1, S2 and S3 into an adjusted pressure profile which is different from the basic pressure profile. Thus, the pressure transition system PSS accomplished a relatively smoothed-out, or fuzzy, pressure profile to be applied to the body part 100. This is advantageous both from a medical and a patient-comfort point-of-view. The pressure transition system PSS, in turn, preferably includes an auxetic-foam composite or other material having a deformable microcellular structure.

FIGS. 23-26 illustrate examples of therapeutic garments 2300, 2400, 2500 and 2600 including the proposed device.

FIG. 23 shows a leg garment 2300, where a plurality of segments S1, S2, . . . , Sn are adapted to enclose both the upper and the lower part of a patients leg. An extensive pressure transition system PTS is adapted to redistribute basic pressure profiles generated by the segments S1, S2, . . . , Sn, so that the entire leg is exerted to adjusted pressure profiles, for example also at joint portions of the leg that are not covered by any segments.

FIG. 24 shows an arm garment 2400, where a plurality of segments S1, S2, . . . , Sn are adapted to enclose a patient's forearm and over arm. Also here an extensive pressure transition system PTS is adapted to redistribute basic pressure profiles generated by the segments S1, S2, . . . , Sn. Thereby, for instance, an elbow portion which for flexibility reasons is not covered by segments may be exerted to pressure. Additionally, the pressure transition system PTS is adapted to extend over the patient's hand in the form of a compression glove 2410, so as to prevent lymphatic fluids from pooling in the hand.

FIGS. 25 and 26 show garments 2500 and 2600 for exerting external pressures to a patient's foot and hand respectively. In both these cases a plurality of segments S1, S2, . . . , Sn are adapted to enclose a said extremities, and a pressure transition system PTS is adapted to redistribute basic pressure profiles generated by the segments S1, S2, . . . , Sn. Thus, basic pressure profiles may be smoothed out and also portions which are not covered by segments may be pressurized.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A device for exerting an external pressure to a human body part, the device comprising at least two segments of which a first segment is adapted to at least partially enclose a first portion of the body part in a form-fitting manner and a second segment is adapted to at least partially enclose a second portion of the body part in a form-fitting manner, each of the at least two segments containing an electroactive-material-based actuator which is adapted to receive an electrical control signal and in response thereto adjust the actuator's morphology so as to in the absence of any intermediate component between the actuator and the body part cause the segment to apply a basic pressure profile to the body part in direct response to the electrical control signal; a pressure transition system which is adapted to be positioned between a first surface defined by the first and second segments and a second surface defined by a body part, the pressure transition system extends over the first and second portions of the body part when the device is fitted on the body part and the pressure transition system has such mechanical properties that the pressure transition system is adapted to redistribute the basic pressure profiles between the first and second segments, in such manner that a control signal in respect of the first segment causes the pressure transition system to apply a first adjusted pressure profile to at least a part of the second portion of the body part, a control signal in respect of the second segment causes the pressure transition system to apply a second adjusted pressure profile to at least a part of the first portion of the body part, and each of the first adjusted pressure profile and the second adjusted pressure profile being different from each of a first basic pressure profile of the first segment and a second basic pressure profile of the second segment;

and wherein the pressure transition system comprises a number of moisture passages adapted to receive and transport exudates from the body part to at least one liquid receptacle.

* * * * *